US012753378B2

(12) United States Patent
Dai et al.

(10) Patent No.: US 12,753,378 B2
(45) Date of Patent: Oct. 6, 2026

(54) DEVICE, A METHOD AND A SYSTEM FOR DISPERSING CELL CLUMPS

(71) Applicant: SUZHOU ETTA BIOTECH CO., LTD., Suzhou (CN)

(72) Inventors: Edward Dai, Suzhou (CN); Shiying Zhu, Suzhou (CN); Nan Qiao, Suzhou (CN)

(73) Assignee: SUZHOU ETTA BIOTECH CO., LTD., Suzhou (CN)

( * ) Notice: Subject to any disclaimer, the term of this patent is extended or adjusted under 35 U.S.C. 154(b) by 733 days.

(21) Appl. No.: 18/140,724

(22) Filed: Apr. 28, 2023

(65) Prior Publication Data

US 2023/0257688 A1 Aug. 17, 2023

Related U.S. Application Data

(63) Continuation of application No. PCT/CN2021/118842, filed on Sep. 16, 2021.

(30) Foreign Application Priority Data

Oct. 28, 2020 (CN) ........................ 202011169801.2

(51) Int. Cl.

| | |
|---|---|
| ***C12M 1/12*** | (2006.01) |
| ***C12M 1/00*** | (2006.01) |
| ***C12M 1/33*** | (2006.01) |
| ***C12M 3/00*** | (2006.01) |
| ***C12N 5/07*** | (2010.01) |

(52) U.S. Cl.

CPC ............ *C12M 23/06* (2013.01); *C12M 23/32* (2013.01); *C12M 23/44* (2013.01); *C12M 45/02* (2013.01); *C12N 5/06* (2013.01); *C12N 2509/00* (2013.01)

(58) Field of Classification Search

CPC ...... C12M 23/06; C12M 23/32; C12M 23/44; C12M 23/2906; C12M 35/04; C12M 45/02; C12N 5/06; C12N 5/0636; C12N 2509/00

See application file for complete search history.

(56) References Cited

U.S. PATENT DOCUMENTS

2012/0258536 A1* 10/2012 Aidun .................... C12M 45/02 435/410
2014/0287509 A1* 9/2014 Sharei .................. C12N 5/0602 435/375
2017/0355950 A1* 12/2017 Zohar .................... C12M 45/02

FOREIGN PATENT DOCUMENTS

CN 205774525 U 12/2016
CN 110366590 A 10/2019
(Continued)

OTHER PUBLICATIONS

International Search Report for PCT/CN2021/1188420 mailed on Dec. 15, 2021.

*Primary Examiner* — Michael L Hobbs
(74) *Attorney, Agent, or Firm* — Schmeiser Olsen PLLC

(57) ABSTRACT

A cell clump dispersing device for dispersing cell clumps is provided, including a dispersion structure module that includes at least one structure for providing fluid flow shear force. Each structure for providing liquid flow shear force includes an inlet for cell clumps to be dispersed to enter the structure, and at least one outlet for dispersed cell clumps to flow out of the structure. A diameter of the outlet is smaller than that of the inlet, and an end of at least one of the structure is capable of being connected to an end of another of the structure.

18 Claims, 6 Drawing Sheets

(56) References Cited

FOREIGN PATENT DOCUMENTS

| | | | |
|---|---|---|---|
| CN | 209702770 | U | 11/2019 |
| CN | 209906780 | U | 1/2020 |
| CN | 110982667 | A | 4/2020 |
| CN | 210620757 | U | 5/2020 |
| JP | 2010094071 | A | 4/2010 |

* cited by examiner

DEVICE, A METHOD AND A SYSTEM FOR DISPERSING CELL CLUMPS

CROSS-REFERENCE TO RELATED APPLICATIONS

This application is a continuation application to PCT Application No. PCT/CN2021/118842, having a filing date of Sep. 16, 2021, which claims priority to CN Application No. 202011169801.2, having a filing date of Oct. 28, 2020, the entire contents both of which are hereby incorporated by reference.

FIELD OF TECHNOLOGY

The following relates to a device, a method and a system for dispersing cell clumps, and more particularly, the present disclosure relates to a device, a method and a system for dispersing cell clumps in a closed tubing by utilizing liquid flow shear force.

BACKGROUND

T cells obtained from activated PBMC are in the form of clumps. However, single cell suspension is needed when electrotransfecting cells in order to obtain higher cell electrotransfection efficiency. In a traditional method, a lab technician is required to use a pipette to blow and aspirate cell clumps in a test tube or centrifuge tube by pressing the pipette repeatedly. Cell clumps passing through the tip are blown-off/aspirated several times utilizing the shear force provided by the liquid ejected from the pipette tip, thereby dispersed into single cells, which is time-consuming and labor-intensive. The above operations are completed on an ultra-clean bench, but the entire process is still in an open environment, and there is still a risk of contamination for cell samples. Especially in the preparation of immune cells for clinical treatment (for patients), it is even more necessary to meet the high standard of zero contamination, and the above potential risks must be completely eliminated. In other words, cell samples must be processed in a closed tubing system, and none of the intermediate links/processing/steps can be operated outside the closed system. In other cases, when the closed tubing system as a whole is subjected to conventional vortex-shaking treatment, cell clumps can be dispersed to a certain extent, but there are still many small cell clumps that cannot be further dispersed into single cells.

Therefore, there is an urgent need for a device to be used in a closed tubing system and to provide fluid flow shear force sufficient to disperse cell clumps into single cells, to meet the needs of the above-mentioned applications.

In the conventional art, patent CN201920216969.0 provided a device for blowing to separate cells, which controls the shear force by adjusting the speed of the peristaltic pump, and automatically blows to separate cells without affecting cell viability. Further, two cell blow-to-separate bottles are arranged to realize cyclic blow-to-separate, utilizing the characteristics of reversible operation of the peristaltic pump. This device puts forward certain requirements for the experimental operating environment (especially for longer blowing time), for which the cap of the cell blowing bottle can be sealed, and a respirator can be used to balance the internal and external pressure of the cell blowing bottle to prevent the cell suspension in the bottle from being polluted when exposed to the air for a long time. However, firstly, the role of the whole device is only broadly summarized as "improving the effect of cell blowing and separating", but it is not clearly indicated that single cell suspension can be finally obtained. Secondly, during the cyclic blowing process, the flow direction of the cell suspension is "sample bottle 1→blow-to-separate bottle 3→blow-to-separate bottle 2→blow-to-separate bottle 3 or collection bottle 4", which makes the operation more complicated and the workflow also prone to errors. Thirdly, the entire device is still in an open working environment during the actual operation so there is still a risk of contamination for the cell suspension in the tube.

Patent CN201822089384.5 provides a cell blow-to-separate device, which controls the blow speed of cell suspension by adjusting the speed of each peristaltic pump, to complete the blow-to-separate treatment of cell suspension in a closed environment, reducing possible contamination from manual operation. However, firstly, the beneficial effect of the whole device only shows that "cell suspension can be blown and dispersed in a closed environment, and cell suspension can be uniformly mixed", but it is not clearly stated that single cell suspension can be finally obtained. Secondly, an important application of the device is that cell suspension can be directly used for subsequent spinner flask culture and large-scale bioreactor culture, so as the whole, the invention is actually a cell culture device, and "cell blowing-to-separate" is just one of the steps. Thirdly, the entire device includes a first container, a second container, a third container, a first hose, a second hose, a third hose, a fourth hose, a fifth hose and a number of peristaltic pumps, and the structure and operation process of the device is relatively complicated. Fourthly, the entire device is still in an open working environment during the actual operation. Even if the first container, the second container and the third container are provided with air filters, during operations such as adding 1 L-10 L of cell culture medium to the third container 3 and adding digested cell suspension to the first container 1, there is still a risk of contamination of the cell suspension in the tube.

In view of application limitations of the above-mentioned conventional art, the present disclosure proposes a device to be used in a closed tubing system and to provide liquid flow shear force sufficient to disperse cell clumps into single cells.

SUMMARY

An aspect relates to a device, a method and a system for dispersing cell clumps by utilizing liquid flow shear force.

A cell clump dispersing device by utilizing fluid flow shear force in a closed tubing, includes a dispersion structure module.

In some embodiments, the dispersion structure module includes a structure for providing liquid flow shear force, the shape of which is a tubular structure with its cross-sectional area changing from large to small. In some embodiments, the structure for providing liquid flow shear force is a conical nozzle.

In some embodiments, the shape of the axial cross section of the structure for providing liquid flow shear force is conical, funnel-shaped, trapezoidal or gourd-shaped, etc., and the shape of the traverse cross section of the structure for providing liquid flow shear force is circular, oval, square, polygon, etc.

In some embodiments, the diameter of the upper cross-section of the structure for providing liquid flow shear force ranges between 2-10 mm.

In some embodiments, the diameter of the lower cross-section of the structure for providing liquid flow shear force ranges between 5 μm-2 mm.

In some embodiments, the axial length of the structure for providing liquid flow shear force ranges between 5-50 mm. In some embodiments, the axial length of the structure for providing liquid flow shear force ranges between 10-20 mm.

In some embodiments, near the tip/liquid-outlet end of the nozzle, one or more circular notches are arranged along the outer circumference/periphery of the pipe wall, and each notch corresponds to a diameter of the lower cross-section of the nozzle, which means that, nozzles with different diameters of the lower cross-section can be obtained by breaking apart the nozzle along the corresponding notch.

In some embodiments, the dispersion structure module includes at least two structures for providing fluid flow shear force.

In some embodiments, the structures for providing liquid flow shear force are arranged in the dispersion structure module in parallel connection, and the structures for providing liquid flow shear force can be used independently of each other.

In some embodiments, the diameters of the lower cross-section of the parallel-connected structures for providing liquid flow shear force may be the same or different.

In some embodiments, the parallel-connected structures for providing fluid flow shear force are sealed connected to a tube by a diverting device.

In some embodiments, the diverting device includes a multi-way connector, etc.

In some embodiments, the type of sealed connection includes non-detachable integral molding manufacturing connection to form an integrated structure between structures for providing liquid flow shear force, sealant connection, welding connection, etc.

In some embodiments, the type of sealed connection includes detachable thread connection, snap connection, tension connection, Luer taper connection, needle-free joint connection, etc.

In some embodiments, the structures for providing liquid flow shear force are arranged in the dispersion structure module in series connection, and the structures for providing liquid flow shear force are sealed connected to each other.

In some embodiments, along the direction of liquid flow, the lower cross-sectional diameters of the series-connected structures for providing liquid flow shear force may be the same or different.

In some embodiments, the two ends of the series-connected structures for providing liquid flow shear force are respectively sealed connected to the tube.

In some embodiments, the type of sealed connection includes non-detachable connection made by integral molding manufacturing connection to form an integrated structure between structures for providing liquid flow shear force, sealant connection, welding connection, etc.

In some embodiments, the type of sealed connection includes detachable thread connection, snap connection, tension connection, Luer taper connection, needle-free joint connection, etc.

A cell clump dispersing device, for dispersing cell clumps, comprises a dispersion structure module that includes at least one structure for providing fluid flow shear force. Each of the structures for providing liquid flow shear force comprises an inlet for cell clumps to be dispersed to enter the structure, and at least one outlet for dispersed cell clumps to flow out of the structure. The diameter of the outlet is smaller than that of the inlet, each structure has a first end and a second end opposite to the first end, the first end of at least one of the structure is capable of being connected to the second end of another of the structure directly.

In some embodiments, in the same structure for providing liquid flow shear force, the diameter of the outlet is much smaller than that of the inlet.

In some embodiments, each of the structures for providing liquid flow shear force comprises a channel part with a proximal end and a distal end respectively located at opposite ends along its length extension direction, and a narrowed part with a first end and a second end respectively located at opposite ends along its length extension direction. In the same structure for providing liquid flow shear force, the distal end of the channel part is connected to the first end of the narrowed part. The proximal end of the channel part is the inlet, the second end of the narrowed part is the outlet, and the inner diameter of the narrowed part gradually decreases from the first end to the second end.

In some embodiments, the inner diameter of the channel part gradually decreases or remains unchanged from the proximal end to the distal end.

In some embodiments, the structure for providing liquid flow shear force further comprises a protective cover for protecting the outlet with a cavity in which the narrowed part is at least partially located, and the protective cover and the channel part are fixed connected or integrally injection molded.

In some embodiments, the inner diameter of the protective cover gradually decreases or remains unchanged from the end close to the channel part to the end away from the channel part.

In some embodiments, the shape of the axial cross section of the narrowed part is conical, funnel-shaped, trapezoidal or gourd-shaped, and the shape of the traverse cross section of the narrowed part is circular, elliptical, square or polygonal.

In some embodiments, a side wall of the narrowed part close to the second end is provided with one or more structural weak portions. In some embodiments, the structural weak portion is ring-shaped.

In some embodiments, the dispersion structure module further comprises a diverting device with at least one diverting inlet and at least two diverting outlets, and each of the diverting outlets is connected to the inlet of the structure for providing fluid flow shear force.

In some embodiments, the dispersion structure module comprises a plurality of series-connected structures for providing fluid flow shear force along the flow direction of cell clumps to be dispersed, wherein two adjacent structures for providing liquid flow shear force are respectively labeled as the first structure for providing liquid flow shear force and the second structure for providing liquid flow shear force, and the end of the second structure for providing liquid flow shear force close to its own inlet is fixed connected to the end of the first structure for providing liquid flow shear force away from its own inlet.

In some embodiments, along the flow direction of cell clumps to be dispersed, the diameters of the outlets of the plurality of series-connected structures for providing fluid flow shear force are the same or decreasing sequentially.

In some embodiments, along the flow direction of cell clumps to be dispersed, two adjacent structures of the plurality of series-connected structures for providing liquid flow shear force are sealed connected.

In some embodiments, each of the structures for providing liquid flow shear force comprises a channel part with a proximal end and a distal end respectively located at opposite ends along its length extension direction, a narrowed part with a first end and a second end respectively located at opposite ends along its length extension directions, and a protective cover with a cavity for protecting the outlet. In the same structure for providing liquid flow shear force, the distal end of the channel part is connected to the first end of the narrowed part. The proximal end of the channel part is the inlet, the second end of the narrowed part is the outlet, and the inner diameter of the narrowed part gradually decreases from the first end to the second end. The narrowed part is at least partially located in the cavity, and the protective cover and the channel part are fixed connected or integrally injection molded. The end of the second structure for providing liquid flow shear force close to its own inlet is fixed connected to the protective cover of the first structure for providing liquid flow shear force.

In some embodiments, each of structures for providing liquid flow shear force comprises a channel part with a proximal end and a distal end respectively located at opposite ends along its length extension direction and a narrowed part with a first end and a second end respectively located at opposite ends along its length extension directions. In the same structure for providing liquid flow shear force, the distal end of the channel part is connected to the first end of the narrowed part. The proximal end of the channel part is the inlet, the second end of the narrowed part is the outlet, and the inner diameter of the narrowed part gradually decreases from the first end to the second end. The end of the second structure for providing liquid flow shear force close to its own inlet is fixed connected to the channel part of the first structure for providing liquid flow shear force.

In some embodiments, the diameter of the inlet of the structure for providing liquid flow shear force ranges between 2-10 mm.

In some embodiments, the diameter of the outlet of the structure for providing liquid flow shear force ranges between 5 μm-2 mm.

In some embodiments, the axial length of the structure for providing liquid flow shear force ranges between 5-50 mm.

In some embodiments, the axial length of the structure for providing liquid flow shear force ranges between 10-20 mm.

A method for dispersing cell clumps in a closed tubing by utilizing fluid flow shear force, comprises a cell clump dispersing device.

A device for dispersing cell clumps into single cells, to be used to disperse cell clumps into single cells, comprises a cell clump dispersing device.

An open tubing system, wherein a channel for flow of liquid containing cell clumps to be dispersed is outward connected, comprises a cell clump dispersing device.

A closed tubing system, wherein a channel for flow of liquid containing cell clumps to be dispersed is closed, comprises a cell clump dispersing device.

In some embodiments, types of cell mainly include cells used for clinical treatment such as PBMC, various types of immune cells (for example, inactivated or activated T cells, NK cells, DC cells, stem cells, etc.), various types of engineered cells such as CHO-S cells, HEK293 cells, etc., and various other biological cells.

The present disclosure has the beneficial technical effect that the cell clump dispersing device of the present disclosure can effectively disperse cell clumps by utilizing liquid flow shear force, provided by the structure for providing liquid flow shear force with a larger diameter inlet and a smaller diameter outlet. Moreover, the cell clump dispersing device of the present disclosure can be used in an open or closed tubing system. Especially when used in a closed tubing system, the operation is simple, the structure for providing liquid flow shear force disperses cell clumps into single cells by utilizing liquid flow shear force, so to obtain single cell suspension, meanwhile the risk of contamination of cell samples is minimized throughout the whole operation process. The device, the method and the system of the present disclosure can be used wherever there is a need to disperse cell clumps. The present disclosure can be applied not only to cell electrotransfection, but also to many other cell processing technologies, such as flow cytometry, single-cell sequencing, immunofluorescence, immunohistochemistry, enzyme-linked immunospotassay (ELISpot) and other cell processing techniques that require single-cell analysis.

BRIEF DESCRIPTION

Some of the embodiments will be described in detail, with references to the following Figures, wherein like designations denote like members, wherein.

Figure 1:
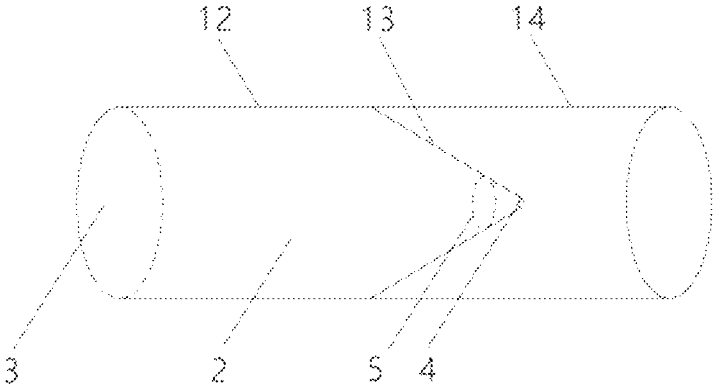
FIG. 1 shows a schematic diagram of a structure for providing liquid flow shear force in a specific embodiment of the present disclosure.

Wherein: 1—first structure for providing liquid flow shear force, 2—second structure for providing liquid flow shear force, 3—inlet, 4—outlet, 5—structural weak portion (notch), 6—a dispersion structure module, 7—tube, 8—diverting device, 9—cell pretreatment device, 10—cell treatment device, 11—pump, 12—channel part, 13—narrowed part, 14—protective cover

DETAILED DESCRIPTION

The present disclosure aims to provide a device that can effectively disperse cell clumps by utilizing liquid flow shear force, which is especially suitable for use in a closed tubing system, and can disperse cell clumps into single cells, thus meeting the needs for cell dispersion under strict contamination prevention conditions in biomedicine, clinical treatment, scientific research, etc. The present disclosure specifically has the following advantages:

1. The cell clump dispersing device of the present disclosure can effectively disperse cell clumps by utilizing liquid flow shear force, using the structure for providing liquid flow shear force with a larger diameter inlet and a smaller diameter outlet, to obtain single cell suspension.
2. The cell clump dispersing device of the present disclosure can be used in an open or closed tubing system, especially when used in a closed tubing system, the operation is simple, and meanwhile the risk of contamination of cell sample is minimized throughout the whole operation process.
3. A plurality of structures for providing liquid flow shear force in the cell clump dispersing device of the present disclosure are detachably connected, which can be flexibly adjusted and freely combined according to actual needs (such as application field, cell type, etc.), and are assembled into different dispersion structure modules by adopting a variety of combined connection modes such as series connection and/or parallel connection.
4. When a plurality of structures for providing liquid flow shear force are series-connected, outlet diameters of the series-connected structures can be decreasing sequentially along the direction of liquid flow, so as to achieve the effect of "stepwise dispersing" of cell clumps, thereby avoiding squeezing and damaging cells when large cell clumps passing through outlets of structures for providing liquid flow shear force with too small diameter.
5. When several structures for providing liquid flow shear force are parallel-connected by diverting devices, the liquid flow of the entire tubing system can be increased, so the overall cell clumps dispersion capacity can be increased.
6. Near the tip/liquid-outlet end of the nozzle (i.e. the second end of the narrowed part) of each structure for providing liquid flow shear force, a plurality of circular notches (i.e. structural weak portions which are ring-shaped.) are arranged along the outer circumference/periphery of the pipe wall, and each notch corresponds to a diameter of the lower cross-section of the nozzle, which means that, nozzles with different diameters of the lower cross-section can be obtained by breaking apart the nozzle along the corresponding notch. The notches can be made in one injection molded, so as to avoid the cost of making molds with different specification, and save the manufacturing cost.

The technical solutions in the embodiments of the present disclosure will be described clearly and completely below. Obviously, the described embodiments are only a part of the embodiments of the present disclosure, rather than all the embodiments. Based on the embodiments of the present disclosure, all other embodiments obtained by those of ordinary skill in the art without creative efforts shall fall within the protection scope of the present disclosure.

Embodiment 1

Figure 2:
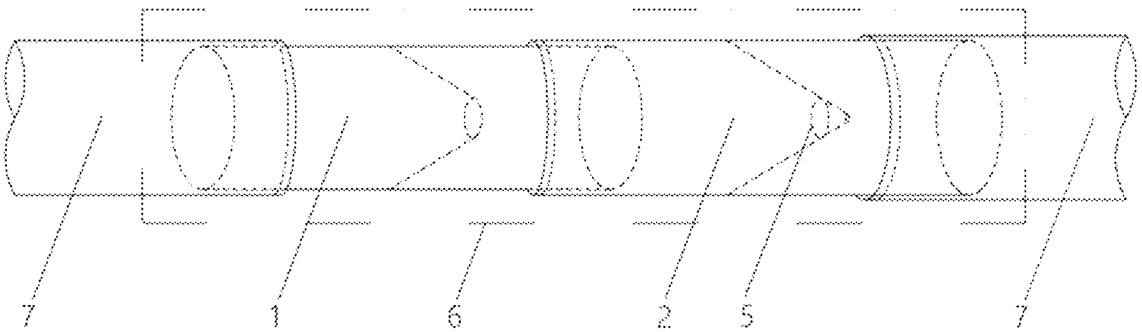
FIG. 2 shows a schematic diagram of a cell clump dispersing device in Embodiment 1 of the present disclosure.

Referring to FIG. 1 and FIG. 2, the present embodiment provides a device for dispersing cell clumps to obtain single cell suspension. The device mainly comprises a dispersion structure module 6 and at least two tubes 7, wherein the dispersion structure module 6 is used for dispersing cell clumps by utilizing liquid flow shear force, and the two tubes 7 are used for connecting the dispersion structure module 6 to the external device. One tube 7 inputs the liquid containing cell clumps to be dispersed to the dispersion structure module 6, and the other tube 7 outputs the liquid containing the dispersed cell clumps, thus forming a complete tubing system, which can be used to obtain single cell suspension.

Specifically, the dispersion structure module 6 includes at least one structure for providing fluid flow shear force. In the present embodiment, the dispersion structure module 6 includes two series-connected structures for providing liquid flow shear force along the flow direction of cell clumps to be dispersed (i.e. the liquid flow direction), labeled as the first structure 1 for providing liquid flow shear force and the second structure 2 for providing liquid flow shear force, respectively. The first structure 1 for providing liquid flow shear force and the second structure 2 for providing liquid flow shear force are basically the same, and both adopt a tubular structure with the cross-sectional area changing from large to small. Specifically, narrowed parts of the two structures for providing liquid flow shear force is in the form of a conical nozzle, the axial cross section is conical, and the traverse cross section is circular. Therefore, they can also be referred to as the first nozzle and the second nozzle, respectively.

Referring to FIG. 1, each structure for providing liquid flow shear force comprises an inlet 3 (also referred to as an upper cross-section) and at least one outlet 4 (also referred to as a lower cross-section). The inlet 3 is for the entry of cell clumps to be dispersed into the structure for providing liquid flow shear force, and the outlet 4 is for the entry of dispersed cell clumps out of the structure for providing liquid flow shear force. The diameter of each outlet 4 is much smaller than that of the inlet 3.

Each of the structures for providing fluid flow shear force includes a channel part 12 with a proximal end and a distal end respectively located at opposite ends along its length extension direction, a narrowed part 13 with a first end and a second end respectively located at opposite ends along its length extension direction, and a protective cover 14. In the same structure for providing liquid flow shear force, the proximal end of the channel part 12 is the inlet 3, the second end of the narrowed part 13 is the outlet 4, and the distal end of the channel part 12 is connected to the first end of the narrowed part 13. The protective cover 14 with a cavity is mainly used to protect the outlet 4, thus the narrowed part 13 is at least partially located in the cavity. The protective cover 14 and the channel 12 can be fixed connected or integrally injection molded.

In this way, the cell clumps to be dispersed enters the structure for providing fluid flow shear force from the proximal end of the channel part 12, enters the narrowed part 13 through the distal end of the channel 12 (i.e. the first end of the narrowed part 13), then flows out from the second end of the narrowed part 13, and flows a short distance in the protective cover 14. After that, it can flow into the next part which can be another structure for providing liquid flow shear force or tube 7.

In order to achieve effective dispersion of cell clumps in the structure for providing fluid flow shear force, the inner diameter of the narrowed part 13 gradually decreases from the first end to the second end, so that the flow velocity of the liquid containing cell clumps in the narrowed part 13 gradually increases, and reaches the maximum when it flows through the outlet 4, thereby dispersing the cell clumps by utilizing fluid flow shear force. The change of inner diameters of the channel part 12 and the protective cover 14 are not particularly required along the direction of liquid flow. In an embodiment, the inner diameter of the channel part 12 gradually decreases or remains unchanged from the proximal end to the distal end, and the inner diameter of the protective cover 14 gradually decreases or remains unchanged from the end close to the channel part 12 to the end away from the channel part 12.

In other embodiments, the shape of the axial cross section of the narrowed part 13 may also be funnel-shaped, trapezoidal, or gourd-shaped, and the shape of the traverse cross section of the narrowed part 13 may also be elliptical, square, or polygonal.

In other embodiments, the same structure for providing fluid flow shear force may also include a plurality of outlets 4, which are spaced arranged at the second end of the narrowed part 13, thereby improving processing efficiency of cell clump dispersion.

Referring further to FIG. 2, in the present embodiment, the end of the second structure 2 for providing liquid flow shear force close to its own inlet 3 is fixed connected to the end of the first structure 1 for providing liquid flow shear force away from its inlet 3. Specifically, the channel part 12 of the second structure 2 for providing liquid flow shear force is fixed connected to the protective cover 14 or the channel part 12 of the first structure 1 for providing liquid flow shear force, and the connected two structures can be sealed by thread connection, snap connection, tension connection, Luer taper connection, needle-free joint connection, etc.

In other embodiments, the dispersion structure module 6 may also include three or more series-connected structures for providing liquid flow shear force along the direction of liquid flow according to actual needs, and the connection mode between two adjacent structures for providing liquid flow shear force is the same as that between the first structure 1 for providing liquid flow shear force and the second structure 2 for providing liquid flow shear force in the present embodiment.

The two structures for providing liquid flow shear force, respectively located at the two ends of the dispersion structure module 6, can be sealed connected to the first and the last tube 7 by thread connection, snap connection, tension connection, Luer taper connection, needle-free joint connection, etc.

It should be noted that, in the series connection mode of the present embodiment, along the direction of liquid flow, the diameter of the outlet 4 of each structure for providing flow shear force is decreasing sequentially. For example, the diameter of the inlet 3 of the first structure 1 for providing flow shear force and the second structure 2 for providing flow shear force are both about 4 mm, the diameter of the outlet 4 of the first structure 1 for providing flow shear force is about 0.5 mm, and the diameter of the outlet 4 of the second structure 2 for providing flow shear force is about 0.2 mm. Therefore, the effect of "stepwise dispersion" of cell clumps can be achieved, avoiding squeezing and damaging cells when large cell clumps pass through too small outlets of structures for providing liquid flow shear force.

Referring to FIG. 1, in addition, in order to provide the above-mentioned plurality of structures for providing fluid flow shear force in which the diameter of the outlet 4 is decreasing sequentially, without adding extra cost, in the present embodiment, one or more structural weak portions 5 are provided near the side wall of the narrowed part 13 of the structure for providing fluid flow shear force near the second end. Specifically, one or more circular notches are provided along the outer circumference/periphery of the pipe wall, which can be easily broken apart by external force. In this way, the first structure 1 for providing liquid flow shear force and the second structure 2 for providing liquid flow shear force can be injection molded by using the same mold. When assembling the dispersion structure module 6, a notch of the upstream first structure 1 for providing liquid flow shear force is broken apart, so that the diameter of the outlet 4 of the first structure 1 for providing liquid flow shear force is larger than the diameter of the outlet 4 of the downstream second structure 2 for providing liquid flow shear force, which makes the actual operation simple, and has significant savings in manufacturing costs.

Embodiment 2

Figure 3:
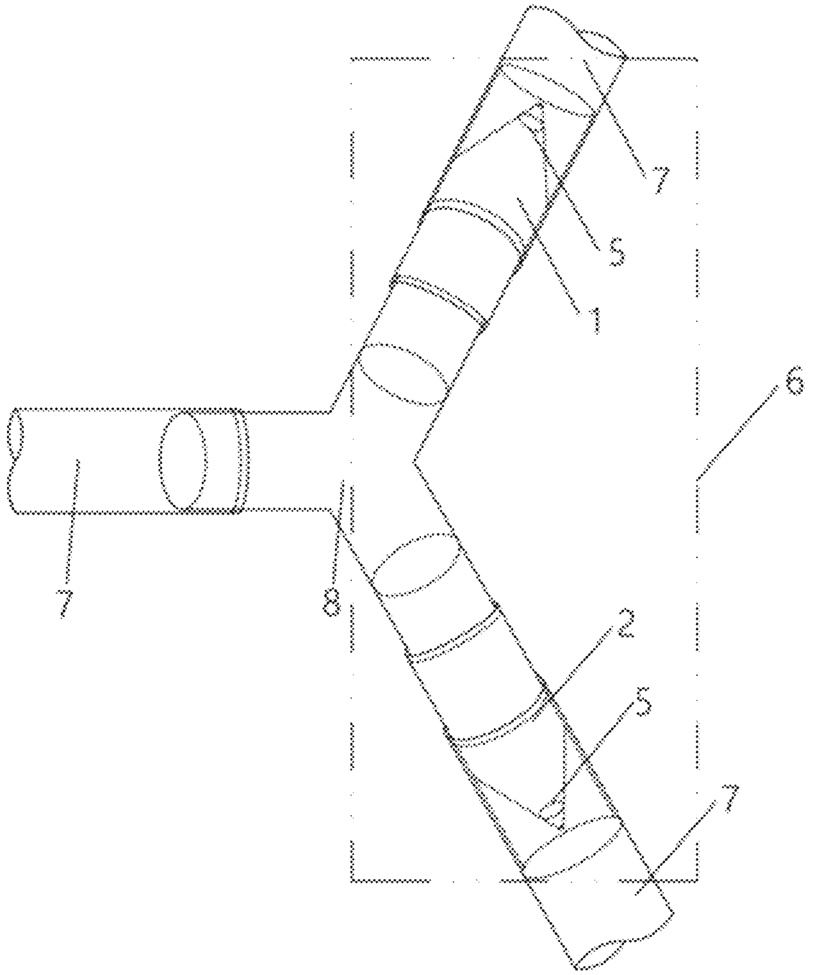
FIG. 3 shows a schematic diagram of a cell clump dispersing device in Embodiment 2 of the present disclosure.

Referring to FIG. 3, the present embodiment provides a device for dispersing cell clumps, similar to the first embodiment, also includes a dispersion structure module 6 and a tube 7. The main difference is that the dispersion structure module 6 in the present embodiment further includes a diverting device 8, so that the first structure 1 for providing liquid flow shear force and the second structure 2 for providing liquid flow shear force are parallel-connected, and correspondingly, there are at least three tubes 7.

In the present embodiment, the diverting device 8 contains a diverting inlet and two diverting outlets, wherein the diverting inlet is connected to a tube 7 available for feeding liquid containing cell clumps to be dispersed into the dispersion structure module 6, and each diverting outlet is connected to the inlet 3 of a structure for providing liquid flow shear force. The outlet 4 of each structure for providing liquid flow shear force is respectively connected to a tube 7 for outputting the liquid containing dispersed cells in two ways. This parallel connection is helpful to increase the liquid flow of the entire tubing system, thus improving overall cell clump dispersion capacity.

In the present embodiment, the diameter of the outlet 4 of the first structure 1 for providing liquid flow shear force is equal to that of the second structure 2 for providing liquid flow shear force, and the liquid can flow out of both outlets 4 at the same flow velocity. The connection between the diverting device 8, the first structure 1 for providing liquid flow shear force, or the second structure 2 for providing liquid flow shear force and the tube 7 is the same as that of the first embodiment.

In the present embodiment, the diverting device 8 is a three-way connector structure, and in other embodiments, the diverting device 8 can also be a four-way, five-way or other structures with more diverting inlets and diverting outlets, which can be specifically arranged according to actual needs.

In other embodiments, parallel and series connections may also be combined, for example, a plurality of structures for providing fluid flow shear force may be series-connected while a plurality of structures providing fluid flow shear force on each branch are parallel-connected.

Embodiment 3

Figure 4:
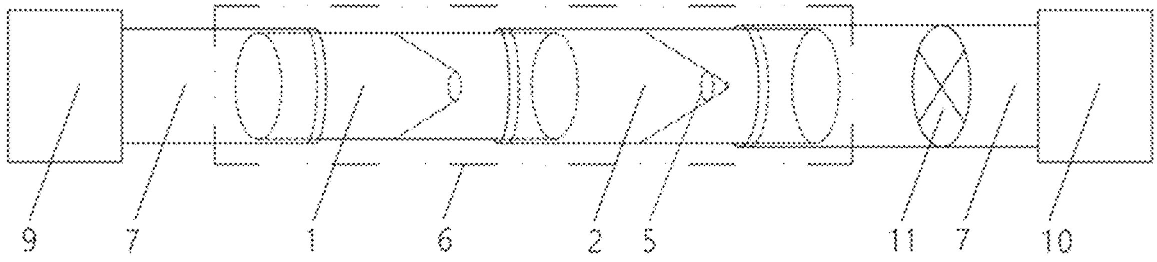
FIG. 4 shows a schematic diagram of a closed tubing system in Embodiment 3 of the present disclosure.

Referring to FIG. 4, the present embodiment provides a closed tubing system in which a channel for flow of liquid containing cell clumps to be dispersed is closed and the system includes the device for dispersing cell clumps in Embodiment 1.

In the present embodiment, along the direction of liquid flow, the closed tubing system further comprises a cell pretreatment device 9 arranged at the front end of the device for dispersing cell clumps, a cell treatment device 10 arranged at the rear end of the device for dispersing cell clumps, and a pump 11 arranged in the tube 7. Both the cell pretreatment device 9 and the cell treatment device 10 are connected to the dispersion structure module 6 through the tube 7.

In the present embodiment, the cell pretreatment device 9 is specifically a T75 cell culture flask, and the cell treatment device 10 is a 50 mL collection tube for receiving the dispersed cell suspension.

The present embodiment further provides a method of using the above-mentioned closed tubing system to disperse cell clumps in a closed tubing by utilizing liquid flow shear force. In embodiments, the method first requires the following preparations:

Day 0: The PBMC frozen in liquid nitrogen are resuscitated and activated with CD3/CD28 monoclonal antibodies in T75 cell culture flasks (i.e. the cell pretreatment device 9).

Figure 5:
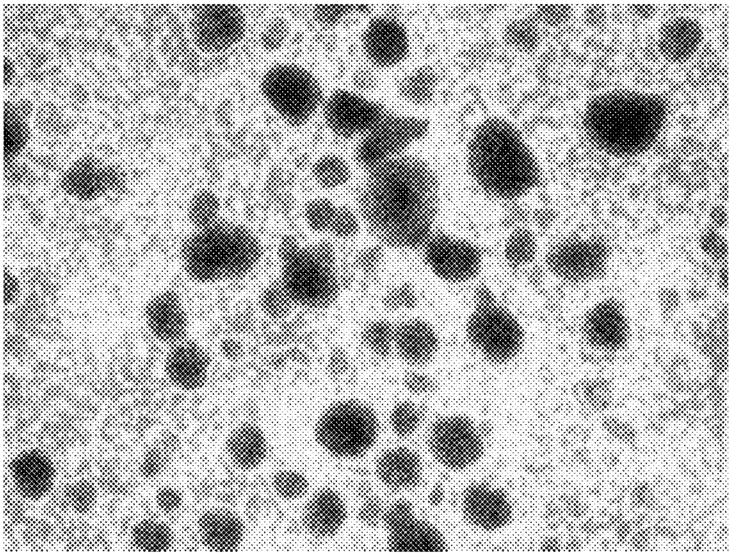
FIG. 5 shows a clumping of T cells after 4 days of activation, in Embodiment 3 and Comparative Embodiments 1 and 2 of the present disclosure.

Day 4: Clumping of activated T cells is observed under a 40× microscope (FIG. 5).

After the preparations are completed, a dispersion experiment can be carried out on cell suspension in the cell pretreatment device 9, and the experimental method specifically includes the following steps:

(1) The pump 11 is turned on, 15 mL of cell suspension containing cell clumps to be treated is aspirated from the cell pretreatment device 9, and flows through the tube 7, the dispersion structure module 6, and the tube 7 in sequence, and finally enters the cell treatment device 10.

(2) According to experimental needs, the treated cell suspension can be transferred from the cell treatment device 10 to the cell pretreatment device 9 again, and the above step (1) can be repeated to perform a new round of dispersion on the cell suspension.

Figure 8:
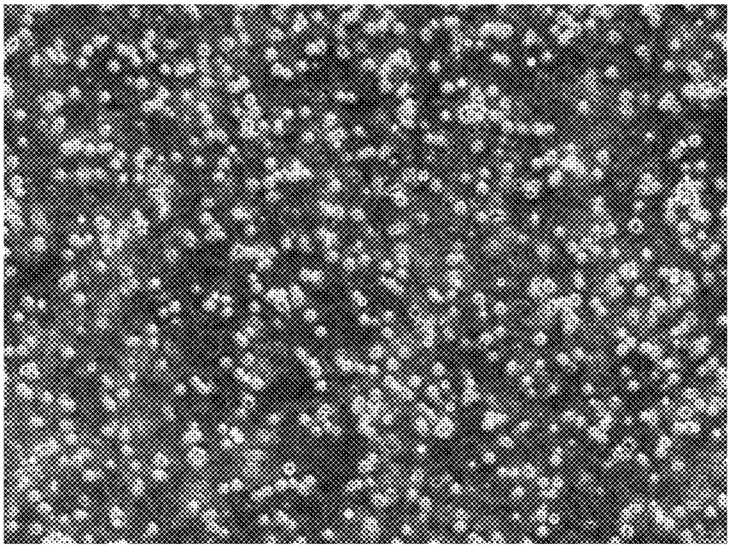
FIG. 8 shows a clumping of T cells after 3 rounds of dispersion experiments on cell suspension in Embodiment 3 of the present disclosure.
Figure 9:
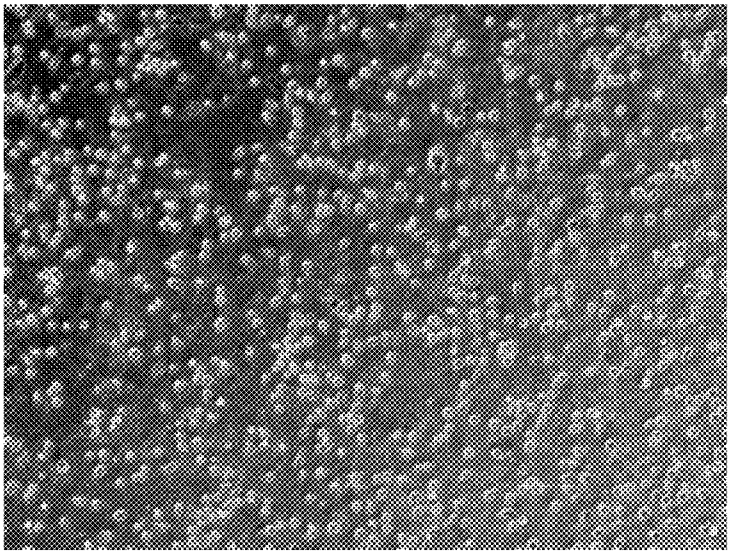
FIG. 9 shows a clumping of T cells after 5 rounds of dispersion experiments on cell suspension in Embodiment 3 of the present disclosure.
Figure 10:
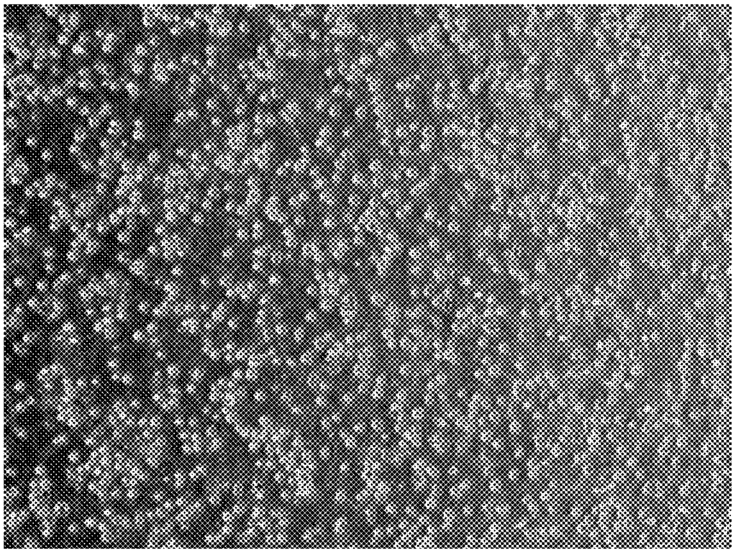
FIG. 10 shows a clumping of T cells after 15 rounds of dispersion experiments on cell suspension in Embodiment 3 of the present disclosure.

(3) Steps (1)-(2) are repeated several times, when the third, fifth, and fifteenth rounds of experiments are completed, and after cell suspension enters the cell treatment device 10 but before entering the next round of experiments, cell suspension in the cell treatment device 10 is sampled, changes of the T cell clumps are observed and photographed under a 200× microscope (FIGS. 8-10).

Comparative Embodiment 1

Figure 6:
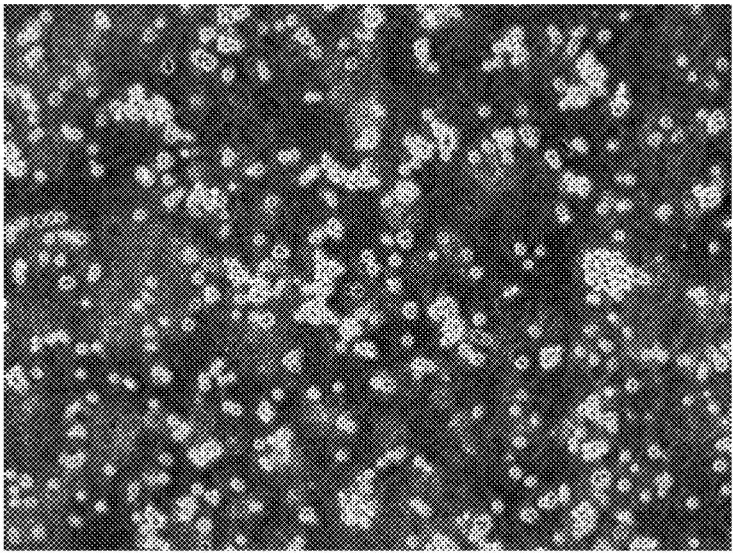
FIG. 6 shows a clumping of T cells after vortex-shaking cell suspension for 10 s in Comparative Embodiment 1 of the present disclosure.
Figure 7:
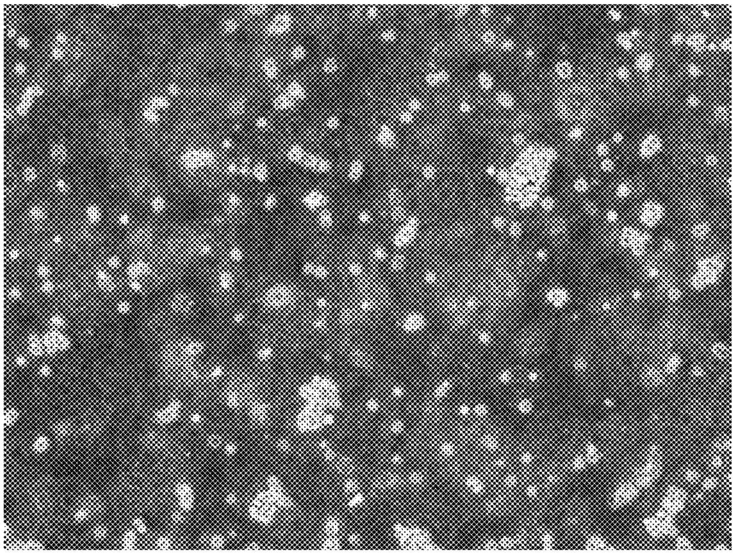
FIG. 7 shows a clumping of T cells clumped after vortex-shaking cell suspension for 15 s in Comparative Embodiment 1 of the present disclosure.

In the present comparative embodiment, the following method is used to disperse T cells after activation on day 4 in Embodiment 3:

(1) 5 mL of cell suspension is aspirated from the T75 cell culture flask into a 15 mL centrifuge tube;

(2) The centrifuge tube is vortex-shaked for 10 s, changes of T cell clumps are observed and photographed under a 200× microscope (FIG. 6);

(3) The vortex-shaking time is extended to 15 s, and changes of T cell clumps are observed and photographed under a 200× microscope (FIG. 7).

Comparative Embodiment 2

Figure 11:
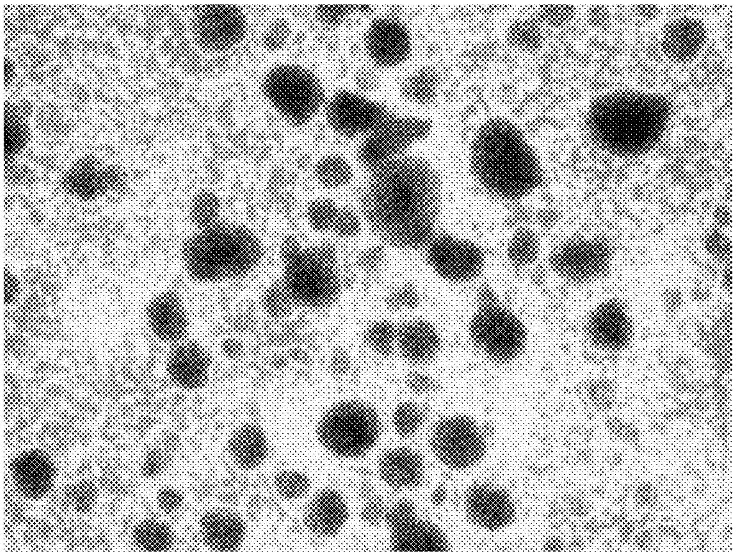
FIG. 11 shows a clumping of T cells after 5 rounds of dispersion experiments on cell suspension in Comparative Embodiment 2 of the present disclosure.

In the present comparative embodiment, the following method is used to disperse T cells after activation on day 4 in Embodiment 3:

(1) The closed tubing system is basically the same as that in Embodiment 3, and the main difference is that the dispersion structure module 6 is replaced with a piece of ordinary tube (the rest of the parts remain unchanged);

(2) Using the same experimental operation steps as in Embodiment 3, 15 mL of cell suspension is passed through the modified closed tubing system. After the fifth round of the experiment, the cell suspension is sampled, changes of T cell clumps are observed and photographed under a 200× microscope (FIG. 11).

The experimental results of above-mentioned Embodiment 3 and Comparative Embodiments 1 and 2 are as follows:

Referring to FIG. 5, FIG. 8 to FIG. 10, in Embodiment 3, after 5 rounds of dispersion experiments by using the closed tubing system, T cell clumps can be dispersed to the greatest extent. And even the number of experiments is increased to 15 rounds, T cell clumps are not appreciably dispersed further.

Referring to FIGS. 5 to 7, in Comparative Embodiment 1, vortex-shaking cell suspension for 10 s can disperse T cell clumps to a certain extent, but there are still many small T cell clumps. Even the vortex-shaking time is further increased to 15 s, T cell clumps are not further dispersed.

Referring to FIG. 5 and FIG. 11, in Comparative Embodiment 2, the closed tubing system without the dispersion structure module 6 cannot effectively disperse cell clumps into single cells.

To sum up, only vortex-shaking cell suspension cannot disperse T cell clumps well into single cells. However, the closed tubing system with the dispersion structure module 6 provided by the present disclosure, can well disperse T cell clumps into single cells by utilizing fluid flow shear force.

Although the present invention has been disclosed in the form of embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

We claim:

1. A cell clump dispersing device for dispersing cell clumps, comprising a dispersion structure module that includes at least one structure for providing fluid flow shear force, the at least one structure for providing fluid flow shear force comprising a first structure for providing liquid flow shear force and a second structure for providing liquid flow shear force that are series-connected along a flow direction of cell clumps to be dispersed, wherein each structure for providing liquid flow shear force comprises an inlet for cell clumps to be dispersed to enter the structure, and at least one outlet for dispersed cell clumps to flow out of the structure, a diameter of the at least one outlet is smaller than that of the inlet, each structure has a first end and a second end opposite to the first end, the first end of at least one of the structure is capable of being connected to the second end of another of the structure directly;

wherein each structure for providing liquid flow shear force comprises a channel part with a proximal end and a distal end respectively located at opposite ends along a length extension direction of the channel part, and a narrowed part with a gradually decreased cross-sectional area in the structure for providing liquid flow shear force and with a first end and a second end respectively located at opposite ends along a length extension direction of the narrowed part, in each structure for providing liquid flow shear force, the distal end of the channel part is connected to the first end of the narrowed part, the proximal end of the channel part is the inlet, the second end of the narrowed part is the outlet, and an inner diameter of the narrowed part gradually decreases from the first end to the second end, an inner diameter of the channel part gradually decreases or remains unchanged from the proximal end to the distal end, the channel part of the second structure for providing liquid flow shear force is fixedly connected to an end of the first structure for providing liquid flow shear force away from the inlet of the first structure.

2. The cell clump dispersing device according to claim 1, wherein the structure for providing liquid flow shear force further comprises a protective cover for protecting the outlet, the protective cover has a cavity in which the narrowed part is at least partially located, and the protective cover and the channel part are fixed connected or integrally injection molded.

3. The cell clump dispersing device according to claim 2, wherein an inner diameter of the protective cover gradually decreases or remains unchanged from an end close to the channel part to an end away from the channel part.

4. The cell clump dispersing device according to claim 1, wherein a shape of an axial cross section of the narrowed part is conical, funnel-shaped, trapezoidal or gourd-shaped, and a shape of a traverse cross section of the narrowed part is circular, elliptical, square or polygonal.

5. The cell clump dispersing device according to claim 1, wherein a side wall of the narrowed part close to the second end is provided with one or more structural weak portions.

6. The cell clump dispersing device according to claim 5, wherein the one or more structural weak portions is ring-shaped.

7. The cell clump dispersing device according to claim 1, wherein the dispersion structure module further comprises a diverting device with at least one diverting inlet and at least two diverting outlets, and each of the diverting outlets is connected to the inlet of the structure for providing fluid flow shear force.

8. The cell clump dispersing device according to claim 1, wherein along the flow direction of cell clumps to be dispersed, diameters of the outlets of the plurality of series-connected structures for providing fluid flow shear force are same or decreasing sequentially.

9. The cell clump dispersing device according to claim 1, wherein along the flow direction of cell clumps to be dispersed, two adjacent structures of the plurality of series-connected structures for providing liquid flow shear force are sealed connected.

10. The cell clump dispersing device according to claim 1, wherein each of the structures for providing liquid flow shear force comprises and a protective cover with a cavity for protecting the outlet, in a same structure for providing liquid flow shear force, the narrowed part is at least partially located in the cavity, and the protective cover and the channel part are fixed connected or integrally injection molded;

wherein the end of the second structure for providing liquid flow shear force close to the inlet of the second structure is fixedly connected to the protective cover of the first structure for providing liquid flow shear force.

11. The cell clump dispersing device according to claim 1, wherein the end of the second structure for providing liquid flow shear force close to the inlet of the second structure is fixedly connected to the channel part of the first structure for providing liquid flow shear force.

12. The cell clump dispersing device according to claim 1, wherein the diameter of the inlet of the structure for providing liquid flow shear force ranges between 2-10 mm, the diameter of the outlet of the structure for providing liquid flow shear force ranges between 5 μm-2 mm, and an axial length of the structure for providing liquid flow shear force ranges between 5-50 mm.

13. The cell clump dispersing device according to claim 12, wherein the axial length of the structure for providing liquid flow shear force ranges between 10-20 mm.

14. A method for dispersing cell clumps in a closed tubing by utilizing fluid flow shear force, comprising using the cell clump dispersing device according to claim 1.

15. An open tubing system, comprising a channel for flow of liquid containing cell clumps to be dispersed is outward connected, wherein the open tubing system further comprising the cell clump dispersing device according to claim 1.

16. A closed tubing system, comprising a channel for flow of liquid containing cell clumps to be dispersed is closed, wherein the closed tubing system further comprising the cell clump dispersing device according to claim 1.

17. A cell clump dispersing device for dispersing cell clumps, comprising a dispersion structure module that includes at least one structure for providing fluid flow shear force, wherein each structure for providing liquid flow shear force comprises an inlet for cell clumps to be dispersed to enter the structure, and at least one outlet for dispersed cell clumps to flow out of the structure, a diameter of the at least one outlet is smaller than that of the inlet, each structure has a first end and a second end opposite to the first end, the first end of at least one of the structure is capable of being connected to the second end of another of the structure directly;

wherein a side wall of the narrowed part close to the second end is provided with one or more structural weak portions.

18. A cell clump dispersing device for dispersing cell clumps, comprising a dispersion structure module that includes at least one structure for providing fluid flow shear force, wherein each structure for providing liquid flow shear force comprises an inlet for cell clumps to be dispersed to enter the structure, and at least one outlet for dispersed cell clumps to flow out of the structure, a diameter of the at least one outlet is smaller than that of the inlet, each structure has a first end and a second end opposite to the first end, the first end of at least one of the structure is capable of being connected to the second end of another of the structure directly;

wherein the dispersion structure module further comprises a diverting device with at least one diverting inlet and at least two diverting outlets, and each of the diverting outlets is connected to the inlet of the structure for providing fluid flow shear force.

* * * * *